United States Patent
Saeki (10) Patent No.: US 12,023,356 B2
(45) Date of Patent: Jul. 2, 2024

(54) STEM CELL FILTRATE PREPARATION AND METHOD FOR PREPARING SAME

(71) Applicant: Masanori Saeki, Okayama (JP)

(72) Inventor: Masanori Saeki, Okayama (JP)

(*) Notice: Subject to any disclaimer, the term of this patent is extended or adjusted under 35 U.S.C. 154(b) by 807 days.

(21) Appl. No.: 15/734,210

(22) PCT Filed: Jul. 3, 2019

(86) PCT No.: PCT/JP2019/026459
§ 371 (c)(1),
(2) Date: Dec. 1, 2020

(87) PCT Pub. No.: WO2020/009147
PCT Pub. Date: Jan. 9, 2020

(65) Prior Publication Data
US 2021/0220406 A1 Jul. 22, 2021

(30) Foreign Application Priority Data
Jul. 4, 2018 (JP) .................... 2018-127901

(51) Int. Cl.
*A61K 35/28* (2015.01)
*A61K 35/35* (2015.01)
*A61K 35/545* (2015.01)

(52) U.S. Cl.
CPC .............. *A61K 35/28* (2013.01); *A61K 35/35* (2013.01); *A61K 35/545* (2013.01)

(58) Field of Classification Search
None
See application file for complete search history.

(56) References Cited

U.S. PATENT DOCUMENTS

| | | | |
|---|---|---|---|
| 2003/0147831 A1 | 8/2003 | Marko | |
| 2007/0292401 A1 | 12/2007 | Harmon et al. | |
| 2010/0047790 A1 | 2/2010 | Southern et al. | |
| 2015/0044179 A1 | 2/2015 | Saeki | |

FOREIGN PATENT DOCUMENTS

| | | | |
|---|---|---|---|
| CN | 101505796 A | 8/2009 | |
| CN | 101610847 A | 12/2009 | |
| CN | 103463128 A | 12/2013 | |
| CN | 104203257 A | 12/2014 | |
| CN | 108126187 A | 6/2018 | |
| EP | 2037963 A2 | 3/2009 | |
| EP | 2125221 A1 | 12/2009 | |
| EP | 2818173 A1 | 12/2014 | |
| JP | 2005519591 A | 7/2005 | |
| JP | 2005519883 A | 7/2005 | |
| JP | 2007509601 A | 4/2007 | |
| JP | 2007533396 A | 11/2007 | |
| JP | 2010265252 A | 11/2010 | |
| JP | 2011132812 A | 7/2011 | |
| JP | 2012181206 A | 9/2012 | |
| JP | 5572777 B2 | 8/2014 | |
| KR | 1020090105937 A | 10/2009 | |
| KR | 101178032 B1 | 8/2012 | |
| KR | 1020140129184 A | 11/2014 | |
| KR | 1020170043196 A | 4/2017 | |
| KR | 101781526 B1 | 9/2017 | |
| WO | 03057152 A2 | 7/2003 | |
| WO | 2007149861 A2 | 12/2007 | |
| WO | 2008075086 A1 | 6/2008 | |
| WO | 2013125674 A1 | 8/2013 | |
| WO | 2014178438 A1 | 11/2014 | |
| WO | 2016072660 A1 | 5/2016 | |

OTHER PUBLICATIONS

Miana VV, González EAP. Adipose tissue stem cells in regenerative medicine. Ecancermedicalscience. Mar. 28, 2018;12:822. doi: 10.3332/ecancer.2018.822. PMID: 29662535; PMCID: PMC5880231. (Year: 2018).*
Doctrow, B. (May 9, 2023). Aging melanocyte stem cells and Gray Hair. National Institutes of Health. https://www.nih.gov/news-events/nih-research-matters/aging-melanocyte-stem-cells-gray-hair#:~:text=Melanocytes%20are%20the%20cells%20that,to%20hair%20graying%20with%20age. (Year: 2023).*
Office Action in Japanese Application No. 2020-529029, mailed Jun. 1, 2021, 10pp.
Office Action in CN application No. 201980033406.0, dated Apr. 24, 2022, 33pp.
Office Action in TW application No. 108123673, dated Apr. 10, 2023, 26pp.
Office Action in Japanese Application No. 2020-529029, mailed Jan. 26, 2021, 7pp.
Office Action in CN application No. 201980033406.0, dated Jul. 25, 2023, 27pp.
Office Action in TW application No. 108123673, dated Jul. 10, 2023, 9pp.
Extended European search report in EP Application No. 19830891.8, dated Jan. 28, 2022, 9pp.

(Continued)

Primary Examiner — Allison M Fox
Assistant Examiner — Alyssa G Weston
(74) Attorney, Agent, or Firm — HAUPTMAN HAM, LLP (57) ABSTRACT

Provided is a stem cell filtrate preparation useful for hair regeneration, alleviation of pain caused by a disease of an interosseous joint, such as osteoarthrosis or rheumatoid arthritis, and treatment of the disease, and in addition, restoration of a damaged muscle, and prevention or treatment of decubitus. The stem cell filtrate preparation according to one aspect of the present invention is characterized by including a filtrate of a stem cell from which a cell membrane is removed. The stem cell may be at least one selected from at least one selected from an adipose-tissue-derived mesenchymal stem cell, an epithelial stem cell, a pigmented stem cell, an iPS cell, and an ES cell. Furthermore, the stem cell filtrate preparation includes an adipocyte or an effective component extracted from cellular fat.

3 Claims, 2 Drawing Sheets

(56) References Cited

OTHER PUBLICATIONS

Yao et al., "Adipose Extracellular Matrix/Stromal Vascular Fraction Gel:A Novel Adipose Tissue-Derived Injectable for Stem Cell Therapy", Plastic and Reconstructive Surgery, Apr. 1, 2017, p. 867-879, vol. 139, No. 4, 2pp.
International Search Report in PCT/JP2019/026459, mailed Jul. 30, 2019. 5pp.
Office Action in JP Application No. 2021-203518, mailed Jan. 9, 2024, 14pp.
Office Action in EP application No. 19830891.8, dated Mar. 20, 2024, 8pp.

\* cited by examiner

STEM CELL FILTRATE PREPARATION AND METHOD FOR PREPARING SAME

RELATED APPLICATIONS

The present application is a National Phase of International Application No. PCT/JP2019/026459 filed Jul. 3, 2019, which claims priority to Japanese Application No. 2018-127901, filed Jul. 4, 2018.

FIELD

The present invention relates to a stem cell filtrate preparation useful for hair regeneration, alleviation of pain caused by a disease of an interosseous joint, such as osteoarthrosis or rheumatoid arthritis, and treatment of the disease, and in addition, restoration of a damaged muscle and prevention or treatment of decubitus.

BACKGROUND

In recent years, hormonal secretion imbalance and the like caused by a change in living environment, stress, and the like, cause many people, regardless of sex, to suffer from thinning hair and hair loss. Therefore, the development of a hair restorer effective for hair growth promotion, hair growth, hair loss prevention, and the like has been increasingly desired and socially required. Various conventional hair restorers containing a low molecular compound, a plant extract, a fermented product of a plant material, or the like have been reported (for example, see Patent Literature 1 (Japanese Patent Application Laid-Open Publication No. 2011-132812) and Patent Literature 2 (Japanese Patent Application Laid-Open Publication No. 2010-265252)). Furthermore, in recent years, hair restorers containing minoxidil, carpronium chloride, trans-3,4'-dimethyl-3-hydroxyflavanone, nicotinamide, piroctone olamine, adenosine, or the like have been put to practical use. However, the conventional hair restorers merely promote the growth of hair papilla cells or activate hair papilla cells, and there is variation in the effects of the conventional hair restorers among individuals. It has thus been said that there is a limit in the ability of the conventional hair restorers.

On the other hand, in recent years, with the advance of regenerative medicine technology utilizing pluripotent stem cells, hair regenerative medicine has been also energetically studied. For example, it has been reported that, using an induced pluripotent stem cell (iPS cell), a tissue "hair follicle" to produce hair was partially regenerated. Furthermore, it has been also reported that a hair follicle can be regenerated by artificially producing a hair follicle prototype from a hair follicle stem cell and transplanting the hair follicle prototype into the skin. Furthermore, it is known that when an adipose tissue and a pre-adipocyte were cultured and a culture medium collected from a culture solution containing the above-mentioned cells was tested for growth-promoting activity on an isolated human hair follicle, hair restoration was promoted (see Patent Literature 3 (Japanese Translation of PCT International Application Publication No. 2005-519591)).

In the case of using such a culture medium collected from the culture solution containing an adipose tissue and a pre-adipocyte (an adipose stem cell), it is necessary to culture a tissue collected from a patient, and therefore it takes a long time to obtain a predetermined cell preparation for hair restoration. In contrast, the inventor of the present invention discloses a cell preparation for hair regeneration that contains an adipocyte and an adipose-tissue-derived mesenchymal stem cell collected from an adipose tissue and does not need cultivation (see Patent Literature 4 (WO 2014/178438)). This cell preparation for hair regeneration is configured such that an adipocyte and an adipose-tissue-derived mesenchymal stem cell coexist, and, when this cell preparation is transplanted into a desired site for hair growth, hair growth is observed in the site, and hair can be regenerated.

Furthermore, as a means for increasing the volume of a human soft tissue, injection of hyaluronic acid, transplantation of an adipocyte, and the like are known and are frequently used in the field of cosmetic surgery, plastic surgery, and the like, such as removal of face wrinkles, excavation treatment, and breast reconstruction. However, although treatment by injection of hyaluronic acid is easy, there is a problem in that the injected hyaluronic acid is absorbed in about half a year, and that thus durability of the effect is poor. In addition, also regarding transplantation of an adipocyte, the adipocyte sometimes becomes necrotic or is absorbed in a living body after transplantation. Thus, there is a disadvantage that reoperation may be required or scar may occur in some cases.

For the purpose of eliminating these disadvantages, transplantation of an adipose stem cell has been proposed, and a method for efficiently separating an adipose stem cell has been developed (for example, see Patent Literature 5 (Japanese Translation of PCT International Application Publication No. 2005-519883) and Patent Literature 6 (Japanese Translation of PCT International Application Publication No. 2007-509601)). By transplanting an adipose stem cell, the fixation ratio of the cell after the transplantation is improved, and a certain effect is recognized in the regeneration of a soft tissue. However, an adipose stem cell obtained by such a method may include impurities in some cases, and there is a possibility that the impurities cause necrosis of an adipocyte or occurrence of a lump (calcification) after transplantation. An adipocyte is generally obtained by liposuction, and sucked fat is a mixture including a wide variety of impurities in addition to the adipocyte and an adipose stem cell. Examples of impurities that should be removed from such a mixture include blood (especially erythrocytes), fatal/vital cells, and senescent cells.

On the other hand, Patent Literature 7 (Japanese Translation of PCT International Application Publication No. 2007-533396) proposes a method by which impurities that could cause calcification or fat necrosis are removed from a mixture collected by liposuction and including an adipocyte and an adipose stem cell, by centrifugation using a syringe equipped with a weight filter, so that a cell preparation (Condensed Rich Fat: CRF (registered trademark)) including a healthy concentrated adipocyte and an adipose stem cell is prepared. By such a method, the fixation ratio of cells is enhanced, and a problem such as generation of a lump hardly occurs, and therefore the method is becoming widely accepted.

As described above, a wide variety of techniques for separation and concentration of an adipocyte and an adipose stem cell have been developed, and an adipocyte and an adipose stem cell that are safe and excellent in fixability have been being provided. As described in Patent Literature 8 (Japanese Patent No. 5572777), a cell preparation containing such an adipocyte and such an adipose stem cell has been used as a cell preparation useful for alleviation of pain caused by a disease of an interosseous joint, such as osteoarthrosis, and treatment of the disease, or as a cell filtrate preparation useful for restoration of a damaged muscle.

CITATION LIST

Patent Literature

Patent Literature 1: Japanese Patent Application Laid-Open Publication No. 2011-132812
Patent Literature 2: Japanese Patent Application Laid-Open Publication No. 2010-265252
Patent Literature 3: Japanese Translation of PCT International Application Publication No. 2005-519591
Patent Literature 4: WO 2014/178438
Patent Literature 5: Japanese Translation of PCT International Application Publication No. 2005-519883
Patent Literature 6: Japanese Translation of PCT International Application Publication No. 2007-509601
Patent Literature 7: Japanese Translation of PCT International Application Publication No. 2007-533396
Patent Literature 8: Japanese Patent No. 5572777

SUMMARY

Technical Problem

With a cell preparation for hair regeneration or cell preparation useful for the alleviation of pain caused by a disease of an interosseous joint, such as osteoarthrosis, and treatment of the disease, a predetermined therapeutic effect can be achieved only by collecting an adipose-tissue-derived mesenchymal stem cell and an adipocyte from a collected crude adipose tissue and making the adipose-tissue-derived mesenchymal stem cell and the adipocyte coexist, without culture treatment. However, the stem cells in these cell preparations are living and capable of further differentiating, and therefore, there is a possibility that, when these cell preparations are transplanted to a predetermined site, the cells proliferate or differentiate on the spot, and have an adverse influence on the transplantation site. In addition, the use of stem cells is subjected to various legal restrictions, and there are constraints so that stem cells cannot be freely used for treatment.

The inventor of the present invention made earnest investigations for solving the problems caused when a cell preparation containing such a stem cell is used, and found that a method in which a cell membrane of a stem cell is removed (hereinafter, sometimes referred to as "destructing a stem cell") and the contents of the stem cell (hereinafter, referred to as a "filtrate". In this state, the filtrate is no longer a stem cell) are used is useful for the hair regeneration and the treatment of a predetermined disease because the filtrate obtained by removing the cell membrane of the stem cell, that is, a stem cell filtrate, contains an effective component secreted from the stem cell that is useful for hair regeneration or the treatment of a predetermined disease, and thus the present invention was completed.

That is, another object of the present invention is to provide a stem cell filtrate preparation capable of hair regeneration; a stem cell filtrate preparation useful for alleviation of pain caused by a disease of an interosseous joint, such as osteoarthrosis, and treatment of the disease; and a stem cell filtrate preparation useful for restoration of a damaged muscle and prevention or treatment of decubitus, the stem cell filtrate preparations having been obtained by removing a cell membrane from a stem cell.

Solution to Problem

A stem cell filtrate preparation according to a first aspect of the present invention is characterized by containing a filtrate of a stem cell from which a cell membrane has been removed.

The filtrate obtained by removing the cell membrane of the stem cell, that is, a stem cell filtrate contains an effective component secreted from the stem cell and useful for hair regeneration or alleviation of pain caused by a disease of an interosseous joint, such as osteoarthrosis, and treatment of the disease, and in addition, restoration of a damaged muscle and prevention or treatment of decubitus. The stem cell filtrate preparation according to the first aspect of the present invention contains such stem cell filtrate, and therefore can achieve a good effect when used for hair regeneration or alleviation of pain caused by a disease of an interosseous joint, such as osteoarthrosis, and treatment of the disease, and in addition, restoration of a damaged muscle and prevention or treatment of decubitus.

Furthermore, the stem cell filtrate preparation according to the first aspect of the present invention does not contain any living stem cells, and therefore, when the stem cell filtrate preparation is transplanted into a predetermined site, a stem cell neither proliferates nor differentiates, and therefore the stem cell filtrate preparation does not have an adverse influence on the transplantation site. In addition, the use of a stem cell is subjected to various legal restrictions, but the stem cell filtrate preparation of the first aspect of the present invention does not contain any living stem cells, and therefore is not subjected to legal restrictions, and can be freely used for various treatments.

Note that a conventionally known pharmaceutically acceptable carrier, excipient, antiphlogistic, analgesic, immunosuppressive, or the like can be added to the stem cell filtrate preparation of the first aspect, if needed. In addition, collagen, a fibroblast, a growth factor, a proliferator, a cytokine, or the like may be added to the stem cell filtrate preparation of the first aspect so long as the effect of the stem cell filtrate preparation is not negated. Alternatively, for example, another cell preparation having the well-known function of regenerating a tissue, such as platelet rich plasma (PRP), may be used in combination with the stem cell filtrate preparation of the first aspect.

In the stem cell filtrate preparation of the first aspect, the stem cell can be at least one selected from an adipose-tissue-derived mesenchymal stem cell, an epithelial stem cell, a pigmented stem cell, an induced pluripotent stem (iPS) cell, and an embryonic stem (ES) cell.

These stem cells are known for their various therapeutic effects of diseases. According to the stem cell filtrate preparation of the first aspect, good effects can be achieved when the stem cell filtrate preparation is used for treatment of various diseases related to stem cells.

Furthermore, at least two selected from an adipose-tissue-derived mesenchymal stem cell, an epithelial stem cell, a pigmented stem cell, an iPS cell, and an ES cell may be mixed and used. In the case of a filtrate of an iPS cell and a filtrate of an ES cell, a sufficient effect can be achieved even using only one of the filtrate of the iPS cell and the filtrate of the ES cell, but, in the case where a filtrate of an adipose-tissue-derived mesenchymal stem cell, a filtrate of an epithelial stem cell, and a filtrate of a pigmented stem cell are added and mixed, a still greater effect can be achieved. Note that, in the case of using only a filtrate of an adipose-tissue-derived mesenchymal stem cell, a filtrate of an epithelial stem cell, and a filtrate of a pigmented stem cell, a combination of two or more of these filtrates brings about a greater effect, and a combination of these three filtrates brings about a still greater effect.

The stem cell filtrate preparation of the first aspect may further contain an adipocyte or an effective component extracted from cellular fat. When the stem cell filtrate preparation contains not only the stem cell filtrate, but also the adipocyte or the effective component extracted from cellular fat, in addition to various therapeutic effects of the stem cell filtrate itself, an effect based on coexistence with the adipocyte or the effective component extracted from cellular fat is enhanced. In particular, the stem cell filtrate preparation can achieve good effects for hair regeneration or alleviation of pain caused by a disease of an interosseous joint, such as osteoarthrosis, and treatment of the disease, or restoration of a damaged muscle and prevention or treatment of decubitus.

Furthermore, when the stem cell filtrate preparation contains an adipocyte, an extracellular matrix (ECM) present around the adipocyte, or the like, sliding of a joint or the like can be improved so that arthralgia can be early alleviated, and pain caused by a disease of an interosseous joint can be alleviated, while, during the alleviation, regeneration of a tissue in the joint, such as a bone tissue, a cartilage tissue, or a soft tissue, by the stem cell filtrate is promoted. In addition, by injecting the stem cell filtrate preparation of the first aspect into an intervertebral disk or the like, the stem cell filtrate preparation functions as a cushion and exhibits an effect of making a motion of a vertebral body better (improvement), and furthermore, the effect of alleviating arthralgia lasts for a long time. In addition, when an adipocyte and the stem cell filtrate are used in combination, the stem cell filtrate is retained in an affected part by an action of the adipocyte, the efficiency of engraftment of the stem cell filtrate and the efficiency of tissue regeneration can be still more enhanced, which leads to still greater effectiveness in the treatment of a disease of an interosseous joint.

In addition, the use of a combination of an adipocyte and the stem cell filtrate has an excellent restoration effect on a degenerated muscle or a muscle damaged by excision of the muscle by surgery, and can early alleviate pain caused by muscle damage, and thus also contributes to improvement of the quality of life (QOL) of a patient. Furthermore, when an effective component extracted from an adipocyte, such as IL-1β, which is inflammatory cytokine, is added to the stem cell filtrate, the stem cell filtrate has the function of suppressing expression of IL-1β inducible protease in a chondrocyte and thereby protecting the cartilage tissue.

Furthermore, a method for preparing a stem cell filtrate preparation according to a second aspect of the present invention is characterized by including the following steps (1) and (2):
 (1) destructing a cell membrane of a stem cell to obtain a component including the destructed cell membrane, a cell nucleus, and cytoplasm, and
 (2) removing the cell membrane from the component obtained at the step (1) to collect a stem cell filtrate.

In the method for preparing the stem cell filtrate preparation of the second aspect, as the stem cell, at least one selected from an adipose-tissue-derived mesenchymal stem cell, an epithelial stem cell, a pigmented stem cell, an iPS cell, and an ES cell can be used. Furthermore, at least two selected from an adipose-tissue-derived mesenchymal stem cell, an epithelial stem cell, and a pigmented stem cell may be mixed. In the case of a filtrate of an adipose-tissue-derived mesenchymal stem cell, a filtrate of an epithelial stem cell, and a filtrate of a pigmented stem cell, a combination of two or more of these filtrates leads to a greater effect, and a combination of these three filtrates leads to a still greater effect. In the case of a filtrate of an iPS cell and a filtrate of an ES cell, a sufficient effect can be achieved even only a filtrate of an iPS cell or a filtrate of an ES cell.

In the method for preparing the stem cell filtrate preparation of the second aspect, the step (1) may be the step of irradiating an adipose tissue collected from a body or an internal adipose tissue with laser light or ultrasonic waves and thereby destructing a cell membrane of a mesenchymal stem cell in the adipose tissue.

In the method for preparing the stem cell filtrate preparation of the second aspect, an adipocyte or an effective component extracted from cellular fat may be added to the stem cell filtrate obtained at the step (2).

According to the method for preparing the stem cell filtrate preparation of the second aspect of the present invention, the stem cell filtrate preparation of the first aspect of the present invention can be prepared easily.

Advantageous Effects of Invention

As described above, the stem cell filtrate preparation of the present invention contains contents of a stem cell, and therefore can achieve good effects when used for hair regeneration or alleviation of pain caused by a disease of an interosseous joint, such as osteoarthrosis, and treatment of the disease, and in addition, restoration of a damaged muscle and prevention or treatment of decubitus. Furthermore, the stem cell filtrate preparation does not contain any living stem cells, and therefore, when the stem cell filtrate preparation is transplanted into a predetermined site, a stem cell neither proliferates nor differentiates, and thus, the stem cell filtrate preparation does not have an adverse influence on the transplantation site. In addition, the use of a stem cell is subjected to various legal restrictions, but the stem cell filtrate preparation of the present invention does not contain any living stem cells, and therefore is not subjected to legal restrictions, and can be freely used for various treatments. Furthermore, according to the method for preparing the stem cell filtrate preparation of the present invention, there can be easily prepared the stem cell filtrate preparation capable of achieving the effects of hair regeneration or alleviation of pain caused by a disease of an interosseous joint, such as osteoarthrosis, and treatment of the disease, and in addition, restoration of a damaged muscle and prevention or treatment of decubitus.

DESCRIPTION OF EMBODIMENTS

Hereinafter, a stem cell filtrate preparation and a method for preparing the same according to the present invention will be described in detail using embodiments. Note that the following embodiments are merely examples to specify technical ideas of the present invention, and are not intended to limit the present invention. The present invention can be equally applied to other embodiments included in the scope of the claims.

Embodiment 1

In Embodiment 1, a stem cell filtrate preparation including a mixture of an adipose-tissue-derived stem cell filtrate and an adipocyte was prepared. The stem cell filtrate preparation of Embodiment 1 is suitable for hair regeneration. Note that the adipose-tissue-derived mesenchymal stem cell mainly means a stem cell capable of differentiating into an adipose tissue, a muscle cell, bone, cartilage, ligament, a skin cell, and a nerve cell.

As the adipose-tissue-derived mesenchymal stem cell to be used in Embodiment 1, a cell collected from an adipose tissue collected from a living body may be used, or a cell contained in an adipose tissue of a living body may be used just as it is. In particular, an adipose-tissue-derived mesenchymal stem cell present in a subcutaneous adipose tissue can be easily collected with a relatively low attack rate, and can also be collected in relatively large amounts, and furthermore can be collected simultaneously with an adipocyte. Therefore, the stem cell filtrate preparation of Embodiment 1 can be prepared by destructing and filtering a membrane of the adipose-tissue-derived mesenchymal stem cell, and mixing the resultant filtrate with a collected adipose tissue just as it is. Note that, in the stem cell filtrate preparation of Embodiment 1, when the amount of a filtrate component corresponding to the adipose-tissue-derived mesenchymal stem cell is larger than the amount of the adipocyte, greater therapeutic effects can be achieved.

Note that the adipocyte (fat cell) is a cell that has functions of synthesizing, storing, and releasing fat, and forms an adipose tissue. In addition, the adipocyte is completely differentiated, and therefore does not undergo cell division. The adipocyte is classified into a white adipocyte and a brown adipocyte. Either of the white adipocyte and the brown adipocyte may be used or a mixture thereof may be used. As the adipocyte, an isolated adipocyte may be used, or a mixture of an ECM present around an adipocyte and the adipocyte may be used. Specifically, an adipose tissue collected as an adipocyte may be used as it is, or what is obtained by removing an extracellular matrix from the collected adipose tissue may be used.

The concentration of the filtrate component corresponding to the adipose-tissue-derived mesenchymal stem cell in the stem cell filtrate preparation of Embodiment 1 is not particularly limited, but, from the viewpoint of efficiently promoting hair regeneration, the concentration of the filtrate component is equivalent to, for example, 10,000 or more, preferably 100,000 or more, more preferably 150,000 or more, and particularly preferably 150,000 to 200,000 pieces of the adipose-tissue-derived mesenchymal stem cells per 1 mL of the stem cell filtrate preparation.

The number of adipocytes in the stem cell filtrate preparation of Embodiment 1 is not particularly limited, but, from the viewpoint of efficiently promoting hair regeneration, the number of adipocytes is, for example, 1,000 or more, preferably 5,000 or more, more preferably, 10,000 or more, and particularly preferably 10,000 to 20,000 per 1 mL of the stem cell filtrate preparation, or a filtrate component concentration corresponding to them.

In the stem cell filtrate preparation of Embodiment 1, the ratio of the number of the filtrate components corresponding to the adipose-tissue-derived mesenchymal stem cell to the number of the adipocytes is not particularly limited. It is thought that a higher content of the filtrate component corresponding to the adipose-tissue-derived mesenchymal stem cell leads to more excellent hair regeneration effects. The filtrate component corresponding to the adipose-tissue-derived mesenchymal stem cell is, for example, at least one time as much as or more than one adipocyte, preferably 100 times as much as or more than one adipocyte, and more preferably about 500 to 1,000 times as much as one adipocyte.

When an adipose-tissue-derived mesenchymal stem cell and an adipocyte that are derived from a patient subjected to administration of the stem cell filtrate preparation is used for the purpose of autologous transplantation in the stem cell filtrate preparation of Embodiment 1, immunorejection can be avoided. However, this does not limit that the stem cell filtrate preparation of Embodiment 1 is prepared using an adipose-tissue-derived mesenchymal stem cell and an adipocyte that are derived from a person other than patients subjected to administration of the stem cell filtrate preparation, and used for allogeneic transplantation. In the case of using an adipose-tissue-derived mesenchymal stem cell and an adipocyte that are derived from a person other than patients subjected to administration of the stem cell filtrate preparation, it is preferable to perform treatment for removing antigenicity, such as gamma irradiation, for the adipocyte (including an ECM existing around the adipocyte) collected from the person before preparation of a filtrate. Although an adipose-tissue-derived mesenchymal stem cell is generally a cell having no immunogenicity, the adipose-tissue-derived mesenchymal stem cell may be subjected to the above-mentioned treatment and used, if needed. Furthermore, the stem cell filtrate preparation can be prepared by culturing an adipose-tissue-derived mesenchymal stem cell and using the cultured adipose-tissue-derived mesenchymal stem cell.

Generally, an adipose tissue includes an adipose-tissue-derived mesenchymal stem cell and an adipocyte, and therefore the stem cell filtrate preparation of Embodiment 1 may be prepared by using a collected adipose tissue as it is, or by using what is obtained by removing impurities (for example, an anesthetic solution to be injected upon collection of fat (what is called tumescent fluid), an aged adipocyte, blood, and tissue fluid) from a collected adipose tissue, what is obtained by removing the impurities and a part of adipocytes from a collected adipose tissue, or the like.

<Other Components>

Furthermore, a conventionally known pharmaceutically acceptable carrier, excipient, antiphlogistic, analgesic, immunosuppressive, or the like can be added to the stem cell filtrate preparation of Embodiment 1, if needed. In addition, collagen, a fibroblast, a growth factor, a proliferator, a cytokine, or the like may be added to the stem cell filtrate preparation of Embodiment 1 so long as the effect of the stem cell filtrate preparation is not negated.

In addition, for example, another cell preparation having a well-known tissue regeneration function, such as platelet rich plasma (PRP), may be used in combination with the stem cell filtrate preparation of Embodiment 1 so long as the effect of the stem cell filtrate preparation is not negated. However, from the viewpoint of further enhancing the efficiency of hair regeneration, it is preferable to remove transforming growth factor $\beta 1$ (TGF $\beta 1$) before use.

Method for Preparing Stem Cell Filtrate Preparation of Experimental Example 1

The stem cell filtrate preparation of Embodiment 1 contains a liquid fraction obtained by filtering a liquid component obtained from an adipose-tissue-derived mesenchymal stem cell, in which the cell membrane has been destructed, or an iPS cell, in which the cell membrane has been destructed, and removing the solid component from the liquid component. Therefore, to prepare the stem cell filtrate of Embodiment 1, the following methods (a) to (c) can be employed.

<Method (a)>
Step (1a) of removing a liquid fraction from an adipose tissue collected from a body to obtain a cell fraction,
Step (2a) of separating an adipose-tissue-derived mesenchymal stem cell and an adipocyte from at least a part of the cell fraction obtained at the step (1a),
Step (3a) of irradiating the separated adipose-tissue-derived mesenchymal stem cell with laser light or ultrasonic waves and thereby destructing a cell membrane of the adipose-tissue-derived mesenchymal stem cell to obtain a liquid component,
Step (4a) of filtering the liquid component obtained at the step (3a) and removing a solid component therefrom to obtain a filtrate of the adipose-tissue-derived mesenchymal stem cell from which the cell membrane has been removed, and
Step (5a) of mixing a part of the adipocyte obtained at the step (2a) with the filtrate of the adipose-tissue-derived mesenchymal stem cell obtained at the step (4a).

<Method (b)>
Step (1b) of, while irradiating an internal adipose tissue with laser light by the use of Lipo Laser (registered trademark) or the like, obtaining a cell fraction containing an adipocyte and an adipose-tissue-derived mesenchymal stem cell, in which the cell membrane has been destructed,
Step (2b) of filtering off a solid component from the adipose-tissue-derived mesenchymal stem cell obtained at the step (1b) and having the destructed cell membrane to obtain a filtrate of the adipose-tissue-derived mesenchymal stem cell,
Step (3b) of obtaining the adipocyte by separation from the cell fraction obtained at the step (1b), and
Step (4b) of mixing the filtrate of the adipose-tissue-derived mesenchymal stem cell obtained at the step (2b) with a part of the adipocyte obtained at the step (3b).

<Method (c)>
Step (1c) of culturing an iPS cell in a culture solution,
Step (2c) of removing a liquid fraction from the culture solution of the step (1c) to obtain a cell fraction,
Step (3c) of separating the iPS cell from at least a part of the cell fraction obtained at the step (2c),
Step (4c) of, by irradiation of the separated iPS cell with laser light or ultrasonic waves, destructing a cell membrane of the iPS cell to obtain a liquid component,
Step (5c) of filtering the liquid component obtained at the step (4c) and removing a solid component therefrom to obtain a filtrate of the adipose-tissue-derived mesenchymal stem cell from which the cell membrane has been removed, and
Step (6c) of adding an adipocyte to the filtrate obtained at the step (5c).

<Details of Method (a)>
The method (a) for preparing the stem cell filtrate preparation of Embodiment 1 includes the steps of:
(1a) removing a liquid fraction from an adipose tissue collected from a body to obtain a cell fraction;
(2a) separating an adipose-tissue-derived mesenchymal stem cell and an adipocyte from at least a part of the cell fraction obtained at the step (1a);
(3a) irradiating the separated adipose-tissue-derived mesenchymal stem cell with laser light or ultrasonic waves and thereby destructing a cell membrane of the adipose-tissue-derived mesenchymal stem cell to obtain a liquid component;
(4a) filtering the liquid component obtained at the step (3a) and removing a solid component therefrom to obtain a filtrate of the adipose-tissue-derived mesenchymal stem cell from which the cell membrane has been removed; and
(5a) mixing a part of the adipocyte obtained at the step (2a) with the filtrate of the adipose-tissue-derived mesenchymal stem cell obtained at the step (4a).

Here, the collected adipose tissue is a mixture of an adipose-tissue-derived cell fraction and an adipose-tissue-derived liquid fraction that are collected from an adipose tissue by liposuction, lipectomy, defatting, or the like. The cell fraction includes an adipocyte, an adipose stem cell, and impurities (hemocytes, fatal/vital cells, senescent cells, and the like). In contrast, the liquid fraction includes a tumescent fluid, a cell tissue fluid, and the like.

The separation of the liquid fraction and the cell fraction can be easily performed by precipitating the cell fraction by leaving the collected fat standing still. Examples of a method for removing the liquid fraction include, but are not particularly limited to, decantation and suction. In addition, centrifugation, filtration, or the like may be performed out, if needed.

Conditions for the centrifugation and the filtration are not particularly limited so long as impurities can be removed without damaging the adipose-tissue-derived mesenchymal stem cell and the adipocyte. For example, the centrifugation and the filtration are performed under conditions of 700 to 2,500×g for 1 to 15 minutes, and preferably 2,000 to 2,200×g for 5 to 10 minutes.

In the case where filtration is performed, for example, blood, tissue fluid, an anesthetic (a tumescent fluid) having been administered to a site from which fat is to be collected, and the like are removed by letting the collected adipose tissue passing through a mesh filter with pores having a size of 10 to 300 μm, preferably 10 to 150 μm, more preferably 10 to 100 μm, further preferably 15 to 20 μm to obtain a mixture of an adipose-tissue-derived mesenchymal stem cell and an adipocyte. Alternatively, a container equipped with such a mesh filter may be charged with the collected adipose tissue containing impurities, and the adipose tissue may be subjected to centrifugation.

Thus, a cell fraction that includes an adipose-tissue-derived mesenchymal stem cell and an adipocyte (including an extracellular matrix) and from which a liquid fraction has been removed can be obtained. At the step (2a), an adipose-tissue-derived mesenchymal stem cell is separated from at least a part of, preferably one-half of the cell fraction obtained at the step (1a). Then, at the step (3a), by irradiating the adipose-tissue-derived mesenchymal stem cell obtained at the step (2a) with laser light or ultrasonic waves, a cell membrane of the adipose-tissue-derived mesenchymal stem cell is destructed to obtain a liquid component. Next, at the step (4a), the liquid component obtained at the step (3a) is subjected to filtration to remove a solid component therefrom, whereby a filtrate of the adipose-tissue-derived mesenchymal stem cell from which the cell membrane has been removed is obtained. Furthermore, at the step (5a), the filtrate of the adipose-tissue-derived mesenchymal stem cell that is obtained at the step (4a) and from which the cell membrane has been removed is added to a part of the adipocyte obtained at the step (2a), whereby the resultant mixture can be used as the stem cell filtrate preparation of Embodiment 1.

Note that the step of culturing the separated adipose-tissue-derived mesenchymal stem cell may be provided after the step (2a).

Alternatively, the step of micronizing the separated adipocyte may be provided after the step (2a). The micronization of the adipocyte can be performed by a method generally employed in the art, and the method is not limited to a particular one, but, for example, the micronization of the adipocyte can be performed by cutting the separated adipocyte with a drill or the like, as necessary. Here, a fine adipocyte means an adipocyte having a size so as to be capable of passing through an injection needle having a gauge of 26 to 30, preferably 18 to 30. Such micronization of the adipocyte can be performed at least once, preferably once to several times, and more preferably once to twice. By micronizing the adipocyte, the concentration of the adipose stem cell per unit volume of the stem cell filtrate preparation can be increased, and thus, not only the effect of hair regeneration, but also the effect of alleviating pain caused by a disease of an interosseous joint or muscle damage, the effect of regeneration of a tissue inside an interosseous joint, and the effect of restoration of a muscle can be still more remarkably achieved.

Here, examples of the method for separating an adipose-tissue-derived mesenchymal stem cell include the method described in Patent Literature 5 (Japanese Translation of PCT International Application Publication No. 2005-519883). More specifically, in order to more easily separate an adipose-tissue-derived mesenchymal stem cell and an adipocyte by decomposing an intercellular junction, a protease is added to a cell fraction. Examples of the protease include collagenase, trypsin, and lipase. One selected from the above-mentioned proteases may be used alone, or two or more of them may be used in combination.

The method for separating an adipose-tissue-derived mesenchymal stem cell and an adipocyte from the cell fraction treated with an enzyme is not particularly limited, and can be appropriately selected from conventionally known methods. Examples of the method may include centrifugation and filtration. Conditions for the centrifugation are not particularly limited so long as the adipose-tissue-derived mesenchymal stem cell and the adipocyte can be separated without damaging these cells. Examples of the centrifugation conditions include centrifugation at 100 to 500×g for 1 to 20 minutes, and preferably 100 to 300×g for 5 to 10 minutes. By subjecting the cell fraction to such centrifugation, an adipose-tissue-derived mesenchymal stem cell can be obtained as a precipitate, and an adipocyte is concentrated in a supernatant.

Then, by making the adipose-tissue-derived mesenchymal stem cell in the precipitate pass through a mesh filter having a pore size of 10 to 100 µm, preferably 10 to 50 µm, and more preferably 15 to 20 µm, the adipose-tissue-derived mesenchymal stem cell can be obtained on the filter, and an adipocyte can be obtained in a filtrate.

The adipocyte and the adipose-tissue-derived mesenchymal stem cell treated with an enzyme is preferably subjected to washing after separation, and the washing can be performed using a phosphate buffer solution (PBS), saline, Ringer's solution, dextran, or the like. The washing may be repeated twice or more times, if needed. Alternatively, upon collecting the cells after the washing, the cells may be subjected to centrifugation if needed. It is beneficial that conditions for the centrifugation follow the conditions employed for the separation of the adipose-tissue-derived mesenchymal stem cell and the adipocyte from the enzyme-treated cell fraction.

Then, when the filtrate resulting from the separation of the adipose-tissue-derived mesenchymal stem cell and containing the adipocyte is filtered using a filter having a smaller pore size, the adipocyte can be separated therefrom and obtained on the filter.

A cell membrane of the thus-separated adipose-tissue-derived mesenchymal stem cell is destructed, for example, using laser or ultrasonic waves, and then a solid component including the destructed cell membrane is filtered by a filter, so that a filtrate of the adipose-tissue-derived mesenchymal stem cell from which the cell membrane has been removed is obtained. Next, the filtrate of the adipose-tissue-derived mesenchymal stem cell from which the cell membrane has been removed and the adipocyte are mixed at a predetermined ratio to obtain the stem cell filtrate preparation of Embodiment 1.

<Details of Method (b)>

The method (b) of preparing the stem cell filtrate preparation of Embodiment 1 includes the steps of:

(1b) while irradiating an internal adipose tissue with laser light by the use of Lipo Laser or the like, obtaining a cell fraction containing an adipocyte and an adipose-tissue-derived mesenchymal stem cell, in which the cell membrane has been destructed;

(2b) filtering off a solid component from the adipose-tissue-derived mesenchymal stem cell obtained at the step (1b) and having the destructed cell membrane to obtain a filtrate of the adipose-tissue-derived mesenchymal stem cell from which the cell membrane has been removed;

(3b) obtaining the adipocyte by separation from the cell fraction obtained at the step (1b); and (4b) mixing the filtrate of the adipose-tissue-derived mesenchymal stem cell obtained at the step (2b) with a part of the adipocyte obtained at the step (3b).

When a cell fraction is extracted from a living body while irradiating an internal adipose tissue with laser light by the use of Lipo Laser, an adipose-tissue-derived mesenchymal stem cell, in which the cell membrane has been destructed, is also obtained as well as the cell fraction.

At the step (2b), a solid component is filtered off from the adipose-tissue-derived mesenchymal stem cell obtained at the step (1b) and having the destructed cell membrane to obtain a filtrate of the adipose-tissue-derived mesenchymal stem cell from which the cell membrane has been removed. Next, the filtrate of the adipose-tissue-derived mesenchymal stem cell obtained at the step (2b) is added to a part of the adipocyte obtained at the step (1b), so that the resultant mixture can be used as the stem cell filtrate preparation of Embodiment 1.

Conditions for the centrifugation are not particularly limited so long as the filtrate can be separated. Examples of the centrifugation conditions include centrifugation at 700 to 2,500×g for 1 to 15 minutes, and preferably 2,000 to 2,200×g for 5 to 10 minutes.

Note that the step of micronizing the adipocyte separated from the cell fraction may be provided after the step (1b). The micronization of the adipocyte can be performed by a method generally employed in the art, and the method for the micronization is not limited to a particular one, but, for example, the micronization can be performed by cutting the separated adipocyte with a drill or the like, as necessary.

Here, a fine adipocyte means an adipocyte having a size so as to be capable of passing through an injection needle having a gauge of 26 to 30, preferably 18 to 30. Such micronization of the adipocyte can be performed at least once, preferably once to several times, and more preferably once to twice. By micronizing the adipocyte, the concentration of the adipose stem cell per unit volume of the stem cell filtrate preparation can be increased, and thus, not only the effect of hair regeneration, but also the effect of alleviating pain caused by a disease of an interosseous joint or muscle damage, the effect of regeneration of a tissue inside an interosseous joint, and the effect of restoration of a muscle can be still more remarkably achieved.

At the step (3b), the adipocyte is obtained by separation from the cell fraction obtained at the step (1b). This step is performed in the same manner as that at the step (2a).

At the step (4b), the filtrate of the adipose-tissue-derived mesenchymal stem cell obtained at the step (2b) and a part of the adipocyte obtained at the step (3b) are mixed to obtain the stem cell filtrate preparation of Embodiment 1.

<Details of Method (c)>

The method (c) includes the steps of:
(1c) culturing an iPS cell in a culture solution;
(2c) removing a liquid fraction from the culture solution of the step (1c) to obtain a cell fraction;
(3c) separating the iPS cell from at least a part of the cell fraction obtained at the step (2c);
(4c) by irradiation of the separated iPS cell with laser light or ultrasonic waves, destructing a cell membrane of the iPS cell to obtain a liquid component;
(5c) by filtration of the liquid component obtained at the step (4c) to remove a solid component therefrom, obtaining a filtrate of the adipose-tissue-derived mesenchymal stem cell from which a cell membrane has been removed; and
(6c) adding an adipocyte to the filtrate obtained at the step (5c).

At the step (1c), an iPS cell is cultured in a culture solution, and, at the step (2c), a liquid fraction is removed from the culture solution of the step (1c) to obtain a cell fraction. At the step (3c), the iPS cell is separated from at least a part of the cell fraction obtained at the step (2c). At the step (4c), by irradiation of the iPS cell obtained at the step (3c) with laser light or ultrasonic waves, a cell membrane of the iPS cell is destructed to obtain a liquid component. Next, at the step (5c), the liquid component obtained at the step (4c) is filtered to remove a solid component therefrom, so that a filtrate of the adipose-tissue-derived mesenchymal stem cell from which a cell membrane has been removed is obtained. Furthermore, at the step (6c), an adipocyte is added to the filtrate obtained at the step (5c), so that the resultant mixture can be used as the stem cell filtrate preparation of Embodiment 1.

Here, as the adipocyte to be added at the step (6c), the adipocyte separated at the step (2a) or the step (3b) can be used. Note that the step (6c) can be skipped, and only the filtrate of the iPS cell at the step (5c) can be used as the stem cell filtrate preparation of Embodiment 1.

In the methods (a) to (c), examples of adding an adipocyte to a stem cell filtrate were described, but, in place of the adipocyte, an effective component extracted from the adipocyte may be added. Examples of the effective component extracted from an adipocyte and added to a stem cell filtrate include an anti-IL-1β antibody, which is anti-inflammatory cytokine, and the anti-IL-1β antibody has the function of suppressing expression of IL-1β inducible protease in a chondrocyte and thereby protecting the cartilage tissue.

<Use and Administration Method>

By administering the stem cell filtrate preparation of Embodiment 1 to the dermis or subcutaneous tissue of a site in which hair regeneration is needed, the stem cell filtrate preparation can promote hair growth in the site and regenerate hair. The stem cell filtrate preparation of Embodiment 1 is capable of remedying thinning hair due to diffuse alopecia, postpartum alopecia, male pattern alopecia, seborrheic alopecia, senile alopecia, alopecia areata, cicatricial alopecia, or alopecia caused by mental illness.

The dose of the stem cell filtrate preparation of Embodiment 1 is appropriately set depending on the amount of hair in an administration site, the sex and physique of a patient, and the like. The concentration of the filtrate of an adipose-tissue-derived mesenchymal stem cell or an iPS cell is not particularly limited, but, from the viewpoint of efficiently promoting hair regeneration, for example, the concentration of the filtration is 10,000 or more, preferably 100,000 or more, more preferably 150,000 or more, and particularly preferably 150,000 to 200,000, in terms of the number of adipose-tissue-derived mesenchymal stem cells or iPS cells contained per 1 mL of the stem cell filtrate preparation of Embodiment 1. Similarly, the concentration of the filtrate is approximately 1,000 to 100,000, preferably approximately 1,000 to 50,000, and more preferably 5,000 to 10,000, in terms of the number of adipocytes contained per 1 mL of the stem cell filtrate preparation of Embodiment 1. The dose of the stem cell filtrate preparation is 0.1 to 1.0 mL, preferably 0.1 to 0.5 mL, and more preferably 0.2 to 0.5 mL, per 1 cm$^2$ of an administration site.

A method for administrating the stem cell filtrate preparation of Embodiment 1 to a site in which hair regeneration is needed is not particularly limited, and a conventionally well-known administration method can be employed. Examples of the administration method include a method of injection with a syringe, a cannula, or the like. Note that, although the hair regeneration effect of the stem cell filtrate preparation of Embodiment 1 varies between individuals, hair growth is usually observed in a site approximately 2 to 6 weeks after administration, and hair regenerates in the site.

<Destruction of Cell Membrane of Adipose-Tissue-Derived Mesenchymal Stem Cell>

In the preparation of the stem cell filtrate preparation of Embodiment 1, laser light or ultrasonic waves are preferably used for the destruction of a cell membrane of an adipose-tissue-derived mesenchymal stem cell. Usually, a predetermined adipose tissue is irradiated with laser light by an optical fiber, so that a cell membrane of an adipose-tissue-derived mesenchymal stem cell is destructed. At this time, when a laser light irradiation device known as Lipo Laser is used, the adipose tissue can be destructed in a wide area at once. A common laser light irradiation device is configured to emit laser light linearly from an irradiation end of an optical fiber. In contrast, Lipo Laser is configured to emit laser light diffusedly at a solid angle of 360 degrees from an irradiation end of an optical fiber.

The ultrasonic destruction of a cell membrane of an adipose-tissue-derived mesenchymal stem cell can be performed using a well-known ultrasonic homogenizer. The ultrasonic destruction of the cell membrane generates and bursts microscopic air bubbles with mechanical energy caused by a probe, and repeatedly applies an intense impact to a cell, thereby crushing the cell. Therefore, during the ultrasonic destruction, heat is easily generated and hence the irradiation is preferably performed in a pulse mode.

Also in the case of using any laser light irradiation device or ultrasonic homogenizer, a cell membrane of an adiposetissue-derived mesenchymal stem cell can be destructed by directly irradiating an adipose tissue or an adipose-tissue-derived mesenchymal stem cell extracted from a living body or an internal adipose tissue with laser light or ultrasonic waves. In particular, a method of directly irradiating an internal adipose tissue with laser light is widely applied to liposuction. In this case, a mixture of a liquid fraction and a cell fraction containing an adipose-tissue-derived mesenchymal stem cell, in which the cell membrane has been destructed, can be obtained directly from a living body.

To collect an adipose-tissue-derived mesenchymal stem cell and an adipocyte directly from a living body tissue, a well-known ultrasonic suction method can be employed, but a cell membrane of the collected adipose-tissue-derived mesenchymal stem cell and a cell membrane of the collected adipocyte are not destructed, and therefore it is necessary to additionally employ the above-mentioned method of destructing a cell membrane with laser light or ultrasonic waves. Note that, as the method of destructing a cell membrane, an example in which a laser light irradiation device or an ultrasonic homogenizer was used was described, but the method is not particularly limited so long as a device configured to emit laser light or ultrasonic waves is used. Furthermore, the method of destructing a cell membrane is not limited to a method in which a device configured to emit laser light or ultrasonic waves is used, and the present invention includes a method of destructing a cell membrane by repeating freezing and thawing once or more times and another method of destructing a cell membrane.

Test Example 1

Hereinafter, actions and effects of the stem cell filtrate preparation of Embodiment 1 will be specifically described using Test Example 1, but the test example should not be construed to limit the stem cell filtrate preparation of Embodiment 1.

(1) Preparation of Stem Cell Filtrate Preparation

For preparation of the stem cell filtrate preparation, LIPOMAX-SC (manufactured by Medikan International Inc., Seoul, Korea) kit was used. At the step of preparing the present stem cell filtrate preparation, it was possible to perform the step without contacting a cell with the open air at all. The specific method is as follows.

Using a syringe (a syringe for LIPOMAX-SC, manufactured by Medikan International Inc., Seoul, Korea), liposuction was performed on each subject. The syringe containing collected fat was left standing still at room temperature (approximately 25° C.) for approximately 10 minutes to separate the fat into a cell fraction and a liquid fraction, and the liquid fraction containing a tumescent fluid was discarded. After that, the syringe was subjected to centrifugation at 2,200×g for 8 minutes. By the centrifugation, the cell fraction was separated into three layers, namely, an upper layer (free oil), an intermediate layer (an adipose-tissue-derived mesenchymal stem cell and an adipocyte), and a lower layer (a liquid fraction such as a cell tissue fluid). After that, only the intermediate layer was left in the syringe, and the upper and lower layers were discarded, whereby a concentrate of the adipose-tissue-derived mesenchymal stem cell and the adipocyte was obtained. Next, the concentrate was separated into the adipose-tissue-derived mesenchymal stem cell and the adipocyte.

Next, the adipocyte was subjected to a gelling treatment to micronize a relatively large adipocyte. The gelling treatment was performed once to three times. A drill (Filler-Geller cutter, manufactured by Medikan International, Inc.) was used for the gelling treatment to cut the adipocyte for micronization, and furthermore, centrifugation was performed at 2,200×g for 5 minutes to obtain a micronized adipocyte.

The adipose-tissue-derived mesenchymal stem cell was sucked into the same syringe as that described above, and irradiated with laser light from Lipo Laser inside the syringe, whereby a cell membrane of the adipose-tissue-derived mesenchymal stem cell was destructed. Next, the syringe was subjected to centrifugation at 2,200×g for 8 minutes. By the centrifugation, the adipose-tissue-derived mesenchymal stem cell was separated into three layers, namely, an upper layer (free oil), an intermediate layer (a solid component including the destructed cell membrane), and a lower layer (a filtrate of the adipose-tissue-derived mesenchymal stem cell). After that, the filtrate was collected, and what was obtained by adding the micronized adipocyte to the filtrate was administered, as the stem cell filtrate preparation of Test Example 1, to an affected part.

Note that, since the adipocyte and the adipose-tissue-derived mesenchymal stem cell were derived from patients and used, the above-mentioned procedures were performed for the patients. The number of cells of a filtrate component corresponding to the adipose-tissue-derived mesenchymal stem cell and the number of cells of a filtrate component corresponding to the adipocyte, both the filtrate components being contained in the obtained stem cell filtrate preparation, vary from one patient to another, but a filtrate component corresponding to approximately 150,000 to 200,000 adipose-tissue-derived mesenchymal stem cells and a filtrate component corresponding to approximately 10,000 to 20,000 adipocytes were contained per 1 mL of the stem cell filtrate preparation.

(2) Confirmation of Hair Regeneration Effect

For two test subjects whose hair was thinning in their foreheads due to alopecia or the like, 2.5 mL of the stem cell filtrate preparation obtained above was hypodermically injected into their right foreheads (approximately 12.5 $cm^2$) having thinning hair, by the use of a syringe.

FIGS. 1A and 1B and FIGS. 2A and 2B respectively illustrate the results of observation of hair growth states in administration sites 2 to 3 months after the stem cell filtrate preparation was administered to Test Subjects A and B. From these results, it was confirmed that the stem cell filtrate preparation containing an adipose-tissue-derived mesenchymal stem cell and an adipocyte had the effect of promoting hair growth in a thinning hair site and regenerating hair.

Embodiment 2

In Embodiment 2, a stem cell filtrate preparation prepared in the same manner as that at the step (c) and containing a filtrate of an adipose-tissue-derived mesenchymal stem cell and an adipocyte was used as a stem cell filtrate preparation for treating a disease in an interosseous joint. Note that, for example, another cell filtrate preparation having a well-known tissue regeneration function, such as PRP, may be used in combination with the stem cell filtrate preparation to be used in Embodiment 2. Furthermore, by adding an angiotensin II receptor antagonist, such as losartan, to PRP, the effect of regeneration of a cartilage tissue can be still further enhanced. However, from the viewpoint of enhancing the efficiency of tissue regeneration, for example, when a cartilage tissue is expected to be regenerated, a vascular endothelial growth factor (VEGF) is preferably removed from PRP before use, in contrast, when bone regeneration is expected, bone morphogenetic proteins (BMPs) are preferably removed before use.

The stem cell filtrate preparation of Embodiment 2 achieves an excellent therapeutic effect on a disease of an interosseous joint. The interosseous joint means a connection part of bones, and encompasses a cartilaginous joint connected by a cartilage or a combination of a cartilage and a fibrous connective tissue, a synovial joint connected by a cartilage and a synovial membrane covering a joint capsule, and a fibrous joint connected by a fibrous connective tissue, however, the interosseous joint used herein especially means a movable part connected by a cartilaginous joint and a synovial joint. Specific examples of the interosseous joint include a vertebral joint, a knee joint, a foot joint, a toe joint, a hip joint, a hand joint, an elbow joint, a shoulder joint, a finger joint, an acromioclavicular joint, and a sacroiliac joint. For example, the interosseous joint encompasses soft tissues, such as a ligament and a meniscus, in the case of a knee joint, and encompasses a disk (intervertebral disk) or the like in the case of a vertebral joint.

Examples of the disease of the interosseous joint include hernia (prolapse), deformation, degeneration, and inflammation. Specific examples of the disease of the interosseous joint include spinal diseases, such as intervertebral disk hernia and spondylosis deformans; joint diseases, such as osteoarthrosis (including hip osteoarthrosis and knee osteoarthrosis) and chronic arthrosis; autoimmune diseases, such as rheumatoid arthritis; and osteonecrosis, such as idiopathic osteonecrosis of knee joint and osteonecrosis of femoral head. Preferable examples of the disease of the interosseous joint include intervertebral disk hernia, osteoarthrosis, chronic arthrosis, idiopathic osteonecrosis of knee joint, and osteonecrosis of femoral head.

The content of a filtrate corresponding to an adipose-tissue-derived mesenchymal stem cell in the stem cell filtrate preparation of Embodiment 2 is not particularly limited so long as a therapeutic effect on the disease of the interosseous joint can be achieved.

It is thought that a higher content of the filtrate corresponding to the adipose-tissue-derived mesenchymal stem cell leads to a still greater therapeutic effect. For example, the content of the filtrate corresponding to the adipose-tissue-derived mesenchymal stem cell per one adipocyte corresponds to at least one or more cells, preferably 5 or more cells, more preferably 1 to 10 cells, and still more preferably 5 to 10 cells. Furthermore, there is preferably a filtrate contained in which the number of the adipose-tissue-derived mesenchymal stem cells contained per 1 mL of the stem cell filtrate preparation of Embodiment 2 is usually 100,000 or more, preferably 150,000 or more, and still more preferably 150,000 to 200,000.

The dose of the stem cell filtrate preparation of Embodiment 2 is not particularly limited so long as a therapeutic effect on the disease of the interosseous joint can be achieved. The dose can be appropriately set depending on the size of an administration site, the site of a disease, the severity of a disease, the sex and physique of a patient, and the like, but, for example, the dose is 0.5 to 20 mL, preferably 1 to 10 mL, and more preferably 1 to 5 mL. Furthermore, for example, to a knee joint, 1 to 20 mL, preferably 1 to 10 mL, and more preferably 5 to 10 mL of the stem cell filtrate preparation of Embodiment 2 can be administered. To an intervertebral disk, 0.5 to 20 mL, preferably 1 to 15 mL, and more preferably 1 to 2 mL of the stem cell filtrate preparation of Embodiment 2 can be administered.

Examples of an administration method include, but are not limited to, a method of injection into a disease site in an interosseous joint (for example, joint space or intervertebral disk (discus intervertebralis)) by the use of a syringe, a cannula, or the like. In addition, stimulating an injection site with a tip of a needle or a cannula upon injection leads to a still greater therapeutic effect. Examples of a method of the stimulation include, but are not particularly limited to, a method of stimulating an injection site by turning a cannula having an obliquely cut tip in all directions upon injecting the stem cell filtrate.

When the stem cell filtrate preparation of Embodiment 2 is administered to patients having these diseases, the stem cell filtrate preparation may be administered after a treatment is given by a well-known method, if needed. For example, in the case of intervertebral disk hernia, the stem cell filtrate preparation of Embodiment 2 can be administered (injected) after removing a prolapsed intervertebral disk by a conventionally well-known method such as percutaneous laser disc decompression (PLDD). By the action of an adipocyte contained in the stem cell filtrate preparation of Embodiment 2, pain caused by a disease of an interosseous joint (arthralgia) is alleviated, and, furthermore, when a mesodermal stem cell is contained, regeneration of a bone tissue, a cartilage tissue, a soft tissue, or the like in the interosseous joint is promoted by the action of the cell.

Furthermore, in the stem cell filtrate preparation of Embodiment 2, the adipocyte obtained by separation from the adipose stem cell at the step (2c) may be washed and then mixed in the stem cell filtrate at the step (5c). The washing can be performed in the same manner as the above-mentioned washing treatment given to the adipose stem cell. Since a healthy and micronized adipocyte is selected and concentrated, the adipocyte obtained here achieves a considerably greater effect in the alleviation of pain caused by a disease of an interosseous joint. Note that the use of the stem cell filtrate preparation prepared by the method of the step (c) was described here, but, also when the stem cell filtrate preparation prepared by each of the methods of the steps (a), (b), (d), and (e) is used, the same excellent effect as that in the case of the step (c) is achieved.

Test Example 2. Effect of Alleviation of Pain Caused by Osteoarthrosis

The stem cell filtrate preparation of Embodiment 2 was administered to a subject having knee osteoarthrosis, and change in the symptom was observed. As a result, the subject to whom the stem cell filtrate preparation of Embodiment 2 had been injected had reduced knee joint pain from the first day of the injection, and the effect lasted for approximately 1 month. In addition, as compared with a subject to whom hyaluronic acid was injected, the effect of alleviation of knee joint pain was clearly expressed from an earlier stage, and the effect of alleviation of pain was also remarkable.

Test Example 3. Effect of Tissue Regeneration on Osteoarthrosis

Figure 1A:
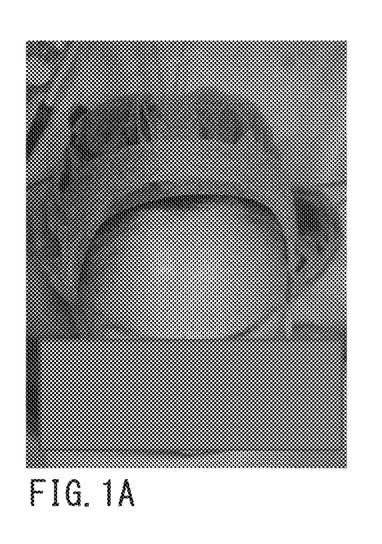
FIGS. 1A and 1B are diagrams illustrating results of observation of hair growth states of subject A's forehead before and after administration of the stem cell filtrate preparation of the present invention, respectively.
Figure 1B:
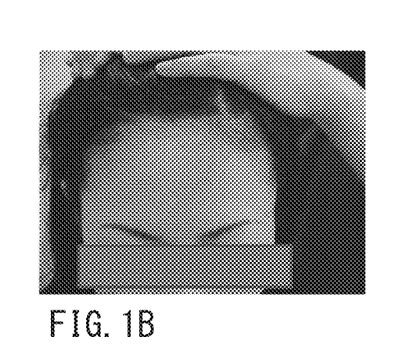
Figure 2A:
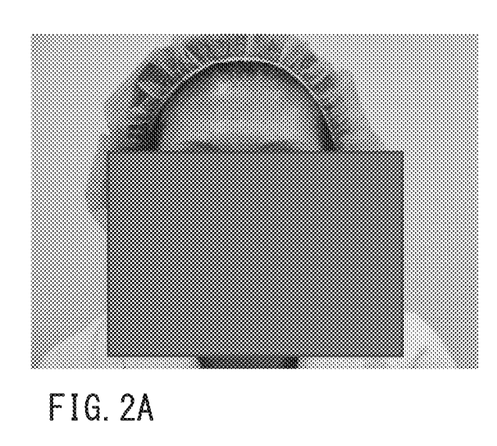
FIGS. 2A and 2B are diagrams illustrating results of observation of hair growth states of subject B's forehead before and after administration of the stem cell filtrate preparation of the present invention, respectively.
Figure 2B:
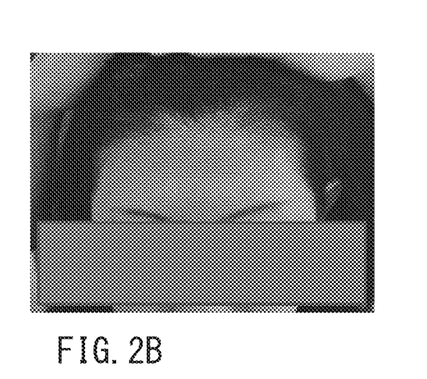
Figure 3A:
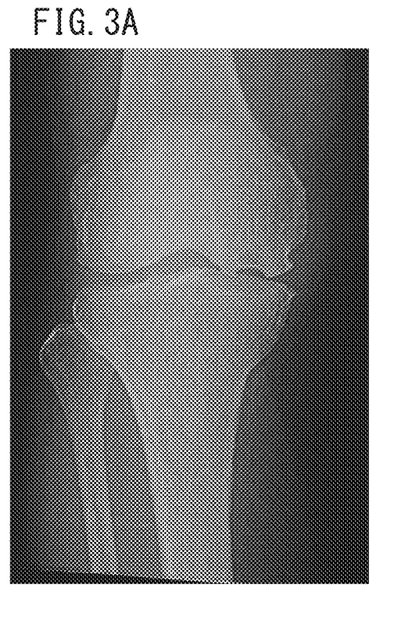
FIG. 3A is a diagram illustrating an X-ray photograph of Subject C's right knee joint before administration of the stem cell filtrate preparation.
Figure 3B:
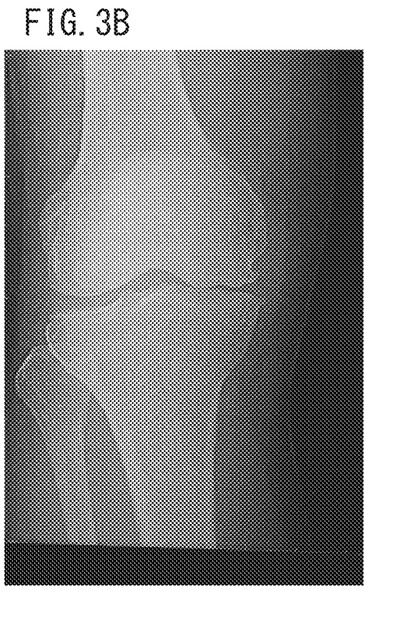
FIG. 3B is a diagram illustrating an X-ray photograph of Subject C's right knee joint approximately 2 months after administration of the stem cell filtrate preparation.

Subject C
  Age at the time of treatment: 66 years old, male
  Anamnesis: medial femoral condyle osteonecrosis (right knee)
  A stem cell filtrate preparation (5 to 10 mL, containing approximately 750,000 to 2,000,000 adipose stem cells) prepared at the step (c) and containing an adipocyte and a filtrate of an adipose-tissue-derived mesenchymal stem cell from which a cell membrane had been removed was injected to Subject C's right knee joint by the use of a cannula having an obliquely cut tip. 5 mL of the stem cell filtrate preparation was injected into the right knee joint. FIGS. 3A and 3B respectively illustrate X-ray photographs of a joint fissure of the outside of Subject C's left knee joint, the X-ray photographs having been taken before the injection of the stem cell filtrate preparation and approximately 2 months after the injection, respectively.

(Results)

Within 5 days after the day of treatment, Subject C had remarkably reduced pain in his knee joint, and the state of improvement in pain lasted even after the elapse of the above-mentioned period, and furthermore, Subject C had remarkable improvement in walking.

Findings from the X-ray photographs about Subject C showed improvement in osteoarthrosis and expansion of joint fissure. Specifically, as illustrated in FIGS. 3A and 3B, the joint fissure of Subject C's right knee joint expanded from the state before treatment illustrated in FIG. 3A to the state approximately 1 month after treatment illustrated in FIG. 3B, and thus the symptom was improved.

The results of Test Example 3 showed that, when the stem cell filtrate preparation containing a filtrate of a stem cell from which a cell membrane had been removed and a filtrate of an adipocyte was injected into a knee joint of Subject C suffering from knee osteoarthrosis, regeneration of a tissue in the knee joint was promoted.

Test Example 4. Effect of Tissue Regeneration Against Osteonecrosis

The stem cell filtrate preparation (5 to 10 mL, containing a filtrate corresponding to approximately 750,000 to 2,000,000 adipose stem cells) prepared at the step (c) and containing a filtrate of a stem cell from which a cell membrane had been removed and an adipocyte was injected into an osteonecrosis site of Subject C in Test Example 3 who additionally developed osteonecrosis in combination with knee osteoarthrosis.

In Subject C, symptoms, that is, walking difficulty, pain, and the like were remarkably improved within 2 days after injection of the stem cell filtrate preparation into a joint. The joint fissure was remarkably improved approximately 2 months after treatment. In addition, a considerable improvement was observed in an image of osteonecrosis 2 months after the injection of the stem cell filtrate preparation into the joint of Subject C.

Test Example 5. Effect of Addition of Anti-IL-1β Antibody as Anti-Inflammatory Cytokine to Stem Cell Filtrate In Test Example 5, use is made of a stem cell filtrate preparation obtained by adding an anti-IL-1β antibody, which is one of effective components extracted from an adipocyte and is anti-inflammatory cytokine, to a filtrate of an adipose-tissue-derived mesenchymal stem cell. When the stem cell filtrate preparation to which the anti-IL-1β antibody had been added is injected into a subject's joint, the stem cell filtrate preparation has the function of suppressing the expression of IL-1β inducible protease in a chondrocyte and thereby protecting the cartilage tissue.

Embodiment 3. Method for Restoring Muscle

In Embodiment 3, the same stem cell filtrate preparation as that used in Embodiment 2 is administered to a muscle damage site of a patient having a damaged muscle. Note that a conventionally well-known pharmaceutically acceptable carrier, excipient, antiphlogistic, analgesic, immunosuppressive, or the like can also be added to the stem cell filtrate preparation for muscular restoration, if needed. Furthermore, collagen, a fibroblast, a growth factor, a proliferator, a cytokine, or the like may be added to the stem cell filtrate preparation of Embodiment 3 so long as the effect of the stem cell filtrate preparation is not negated.

Similarly, for example, another cell filtrate preparation having a well-known tissue regeneration function, such as PRP, may be used in combination with the stem cell filtrate preparation of Embodiment 3 so long as the effect of the stem cell filtrate preparation is not negated. However, from the viewpoint of still further enhancing the efficiency of regeneration of a muscle tissue, it is preferable to remove transforming growth factor β1 (TGF β1) before use.

The stem cell filtrate preparation of Embodiment 3 achieves an excellent effect in muscle restoration when applied to a site of muscle damage. The muscle damage includes myodegeneration, myofibrosis, destruction or necrosis of a muscle fiber, amyotrophy, muscular paralysis, muscle weakness, and the like, and in addition, includes a case in which a muscle has been excised by surgery, injury or the like. In addition, examples of the site or kind of muscle to which the stem cell filtrate preparation of Embodiment 3 is applied include, but are not particularly limited to, skeletal muscles such as trunk muscles, (including an upper or lower limb muscle and pectoralis major); smooth muscles, such as bladder sphincter; and a myocardium. For example, by administering the stem cell filtrate preparation of Embodiment 3 to a damage site of an upper limb muscle, pain due to muscle damage can be early alleviated, and furthermore the muscle is restored, whereby a range of motion (ROM) of the upper limb is expanded or the motor function of the upper limb is improved.

In addition, by administering the stem cell filtrate preparation of Embodiment 3 to a bladder sphincter of a patient having a urination disorder, such as urinary incontinence or frequent urination, due to a decrease in muscle strength, damage, or the like of the bladder sphincter, problems of urinary incontinence, involuntary urination, and the like can be safely and easily eliminated by increasing the muscle strength of the bladder sphincter. In addition, the stem cell filtrate preparation of Embodiment 3 can also be applied to a muscle damage site of a patient having a muscular disease, such as myocardial infarction, ischemia-reperfusion injury, muscular dystrophy (for example, Duchenne's muscular dystrophy (DMD)), or myositis (myopathy).

In addition, a muscle damage is often painful, but the pain can be early alleviated by administering the stem cell filtrate preparation of Embodiment 3 to a muscle damage site. Without expecting limitative interpretation of the present invention, it is thought that such effect of alleviation of pain is owing to the combined effect of a stem cell filtrate contained in the stem cell filtrate preparation of Embodiment 3 and an adipocyte.

The dose of the stem cell filtrate preparation of Embodiment 3 when the stem cell filtrate preparation is used for the purpose of muscle restoration is not particularly limited so long as the effect of muscle restoration can be achieved, and the dose can be appropriately set depending on the size of an administration site, the site of a disease, the severity of a disease, and the sex and physique of a patient, and the like. For example, the dose per unit volume of 10 mL of damaged muscle corresponds to a filtrate having 100,000 to 4,000,000 stem cells, preferably 200,000 to 2,000,000 stem cells, and more preferably 200,000 to 1,000,000 stem cells, in terms of the number of stem cells. In addition, in the case of using a stem cell filtrate preparation obtained by a method including the step (b), for example, the dose per unit volume of 10 mL of a damaged muscle is 0.5 to 20 mL, preferably 1 to 10 mL, and more preferably 1 to 5 mL.

The administration method of the stem cell filtrate preparation of the present invention when the stem cell filtrate preparation is used for the purpose of muscle restoration is not particularly limited, and a conventionally well-known administration method can be employed. Examples of the administration method include a method of injection to a muscle damage site with a syringe, a cannula or the like. Note that, by using the stem cell filtrate preparation prepared by any of the methods (a) to (e), an excellent effect in muscle restoration is achieved.

In Embodiments 1 to 3, examples of using the stem cell filtrate preparation containing a stem cell filtrate and an adipocyte were given, but the present invention is not limited to them, and is applicable to any of a case in which only a stem cell filtrate is used, a case in which a stem cell filtrate preparation contains a stem cell filtrate and an effective component extracted from an adipocyte is used, and a case in which two or more kinds of stem cell filtrates are used. In all the cases, the same remarkable therapeutic effect as those described in Embodiments 1 to 3 can be achieved. For example, also when only a filtrate of an adipose-tissue-derived mesenchymal stem cell is used or also when only a filtrate of an iPS cell is used, a remarkable therapeutic effect can be achieved.

Note that, although examples of using the stem cell filtrate preparation of the present invention for the purpose of muscle restoration were given here, the use of the stem cell filtrate preparation of the present invention can also bring about a remarkable therapeutic effect in prevention or treatment of decubitus. For example, for treatment of decubitus, it is beneficial that the stem cell filtrate preparation of the present invention is applied alone or in combination with a well-known therapeutic agent for decubitus to a site to be treated, thereby protecting the affected site. For prevention of decubitus, it is beneficial that the stem cell filtrate preparation of the present invention is applied alone or in combination with a well-known moisturizing agent or the like to a site in which decubitus tends to easily occur.

In Embodiments 1 to 3, examples of using the stem cell filtrate preparation containing a stem cell filtrate and an adipocyte were given. However, the present invention is not limited to this stem cell filtrate preparation. Even when a stem cell filtrate preparation contains only a filtrate of at least one selected from an adipose-tissue-derived mesenchymal stem cell, an epithelial stem cell, a pigmented stem cell, an iPS cell, and an ES cell, from which a cell membrane has been removed, or even when a stem cell filtrate preparation is obtained by adding an adipocyte or an effective component extracted from the adipocyte to the above-mentioned filtrates, or even when a stem cell filtrate preparation is obtained by mixing two or more selected from the above-mentioned filtrates and a filtrate of the adipocyte or an effective component extracted from the adipocyte, the stem cell filtrate preparation can achieve a predetermined therapeutic effect in accordance with the type of each of the stem cells. For example, also in the case of using an iPS cell, a remarkable therapeutic effect is achieved. The adipose-tissue-derived mesenchymal stem cell, the epithelial stem cell, the pigmented stem cell, the iPS cell, and the ES cell may result from cultivation. Furthermore, for example, at least two selected from an adipose-tissue-derived mesenchymal stem cell, an epithelial stem cell, and a pigmented stem cell may be mixed. In the case of a filtrate of an adipose-tissue-derived mesenchymal stem cell, a filtrate of an epithelial stem cell, and a filtrate of a pigmented stem cell, the use of two or more of these filtrates in combination brings about a greater effect, and the use of three or more of these filtrates in combination brings about a still greater effect. Furthermore, in the case of a filtrate of an iPS cell or a filtrate of an ES cell, only one of the filtrates brings about a sufficient effect, but, in addition, an adipocyte or an effective component extracted from cellular fat can be added to the filtrate.

The invention claimed is:

1. A stem cell filtrate preparation for use in at least one of a method of treating an adipose tissue or skin cell, alleviation of pain caused by a disease of an interosseous joint, or a method of treating a disease of the interosseous joint, comprising:
    (a) a filtrate of an adipose-tissue-derived mesenchymal stem cell from which a cell membrane has been removed;
    (b) a micronized adipocyte; and
    (c) at least one of an anti-IL-1β antibody, a cytokine, a collagen, an extracellular matrix, a fibroblast, a growth factor, a proliferator, or an immunosuppressive.

2. A method for preparing a stem cell filtrate preparation for use in at least one of a method of treating an adipose tissue or skin cell, alleviation of pain caused by a disease of an interosseous joint, or a method of treating the disease of the interosseous joint, the stem cell filtrate preparation comprising:
    (a) a filtrate of an adipose-tissue-derived mesenchymal stem cell from which a cell membrane has been removed;
    (b) a micronized adipocyte; and
    (c) at least one of an anti-IL-1β antibody, a cytokine, a collagen, an extracellular matrix, a fibroblast, a growth factor, a proliferator, or an immunosuppressive, the method comprising:
    (1) destructing a cell membrane of a stem cell to obtain a component including the destructed cell membrane, a cell nucleus, and cytoplasm;
    (2) removing the cell membrane from the component obtained in (1) to collect a stem cell filtrate; and
    (3) mixing the stem cell filtrate obtained in step (2) with the micronized adipocyte and at least one of the anti-IL-1β antibody, the cytokine, the collagen, the extracellular matrix, the fibroblast, the growth factor, the proliferator, or the immunosuppressive to obtain the stem cell filtrate preparation.

3. The method according to claim 2 wherein (1) is a step of destructing the cell membrane of the adipose-tissue-derived mesenchymal stem cell by at least one selected from a method of irradiating an adipose tissue extracted from a body or an adipose tissue in a body with laser light or ultrasonic waves or a method of repeating freezing and thawing, at least once, of the adipose tissue extracted from a body to destruct a cell membrane of a mesenchymal stem cell in the adipose tissue.

* * * * *